United States Patent [19]

Casey et al.

[11] 4,438,253
[45] Mar. 20, 1984

[54] POLY(GLYCOLIC ACID)/POLY(ALKYLENE GLYCOL) BLOCK COPOLYMERS AND METHOD OF MANUFACTURING THE SAME

[75] Inventors: Donald J. Casey, Ridgefield; Kenneth R. Huffman, Stamford, both of Conn.

[73] Assignee: American Cyanamid Company, Stamford, Conn.

[21] Appl. No.: 441,306

[22] Filed: Nov. 12, 1982

[51] Int. Cl.$^3$ ............................................. C08G 63/06
[52] U.S. Cl. .................................. 528/86; 128/92 C; 128/335; 128/335.5; 128/348.1; 525/408; 525/450
[58] Field of Search ................... 528/86; 525/408, 450; 128/92 C, 335, 335.5, 348

[56] References Cited

U.S. PATENT DOCUMENTS

| | | | |
|---|---|---|---|
| 2,917,410 | 12/1959 | Vitalis | 117/138.8 |
| 3,636,956 | 1/1972 | Schnieder | 128/335.5 |
| 3,714,125 | 1/1973 | Shima et al. | 260/75 M |
| 3,784,585 | 1/1974 | Schmitt et al. | 528/303 X |
| 4,048,256 | 9/1977 | Casey et al. | 260/860 |
| 4,070,347 | 1/1978 | Schmitt | 260/77.5 D |
| 4,243,775 | 1/1981 | Rosensaft et al. | 525/415 |

OTHER PUBLICATIONS

Reed, et al., "Trans. Am. Soc. Artif. Intern. Organs", 1977, p. 109, *Biodegradable Elastomeric Biomaterials—Polyethylene Oxide/Polyethylene Terephthalate Copolymers*.

Primary Examiner—Earl A. Nielsen
Attorney, Agent, or Firm—Charles F. Costello, Jr.

[57] ABSTRACT

Multiblock copolymers having the following general formula:

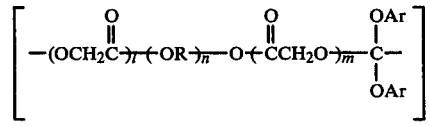

where R represents alkylene and Ar is an aromatic group, are obtained by transesterification of poly(glycolic acid) and an hydroxyl-ended poly(alkylene glycol) such as poly(oxyethylene) in the presence of a catalyst with the degree of polymerization of the copolymer being increased by the subsequent addition of an aromatic orthocarbonate such as tetra-p-tolyl orthocarbonate. The copolymers find use in the manufacture of surgical articles, particularly absorbable monofilament sutures possessing the desired characteristics of flexibility, resulting in good handling properties, and biodegradability.

12 Claims, No Drawings

POLY(GLYCOLIC ACID)/POLY(ALKYLENE GLYCOL) BLOCK COPOLYMERS AND METHOD OF MANUFACTURING THE SAME

CROSS REFERENCE TO RELATED APPLICATIONS

U.S. patent application Ser. No. 441,307, filed Nov. 12, 1982, assigned to the assignee of the present application, discloses poly(glycolic acid)/poly(oxyalkylen) triblock copolymers manufactured by reacting glycolide with a purified hydroxyl-ended poly(alkylene glycol). The copolymers produced there are, it is theorized, triblocks having the structure ABA in which A represents a poly (glycolic acid) block and B represents a poly (oxyalkylene) block.

BACKGROUND OF THE INVENTION

This invention relates to copolymers and, more particularly, to a triblock copolymer based on poly(-glycolic acid) and absorbable surgical articles, including a flexible monofilament suture or ligature manufactured from the copolymer.

Synthetic absorbable sutures manufactured from polyglycolic acid are well known and have met with commercial success. Generally, such sutures are manufactured, sold and used as braids. However, some surgeons prefer the suturing characteristics of a monofilament suture. It has long been recognized that a need exists for an absorbable monofilament suture which exhibits the advantageous properties of strength, flexibility and absorbability possessed by polyglycolic acid braided sutures.

There have been various prior art suggestions for modifying polyglycolic acid, such as by copolymerization of glycolide monomer with other monomers, to produce a polymer possessing the requisite properties desired in a monofilament suture. For example, U.S. Pat. No. 4,243,775, Rosensaft and Webb, assigned to the assignee of the present invention, discloses a polymer material useful for forming both an absorbable braided suture and, under certain conditions, flexible monofilament suture with extended strength retention. That patent discloses the sequential addition of a cyclic ester monomer, such as a lactide, lactone, oxalate or carbonate, to glycolide monomer in the copolymerization process. Triblock copolymers with lactic acid units predominantly on both ends of a glycolide polymer chain are disclosed as are copolymers of trimethylene carbonate and glycolide and monofilament sutures made therefrom.

Other copolymers for use as bioabsorbable materials have been disclosed. U.S. Pat. No. 4,048,256, assigned to the assignee of the present invention, discloses a normally solid bioabsorbable hydrolyzable polymeric reaction product of a polyglycolic acid composition and a polyester of diglycolic acid and an unhindered glycol. Copolymers of 1(−)lactide with glycolide have also been used as suture material as disclosed in U.S. Pat. No. 3,636,956. Polyethylene oxide/polyethylene terephthalate copolymers have been disclosed as biodegradable elastomeric biomaterials in Reed, et al., "Trans. Am. Soc. Artif. Intern. Organs", 1977, page 109. The production of copolymers based on monomers formed from lactic acid or glycolic acid has been known for nonbiological purposes. U.S. Pat. No. 2,917,410 discloses the condensation of glycolic acid with a polyethylene glycol mixture to form an ester with an average molecular weight of 5105 for treating fabric for improved tear strength and abrasion resistance. The addition of aromatic orthocarbonates during the formation of a fiber-forming polyester by the reaction of a dicarboxylic acid or its functional derivative with a glycol is disclosed in U.S. Pat. No. 3,714,125.

U.S. Pat. No. 4,070,347 discloses poly(orthoester) co- and homopolymers and poly(orthocarbonate) co- and homopolymers useful for forming delivery devices with drug dispersed therein for release by controlled polymeric erosion over a prolonged period of time. Glycolide and ethylene glycol are reacted to form an oligomer which is polymerized by condensation with various monomers to yield the desired polymers. The copolymers contain only isolated oxyethylene connecting groups and the orthocarbonate units contain ring structures.

In order to produce an acceptable synthetic absorbable suture, monofilament fibers manufactured from a copolymer must meet certain requirements besides absorbability including good handling properties, adequate tensile and knot strength, avoidance of unfavorable tissue reactions, ability to be sterilized without significantly affecting desired properties and controllable uniformity in the desired properties. The acceptability of a suture is frequently determined by the Youngs modulus (a measurement of flexibility), the tensile strength and the percent elongation at the breaking point (a measure of extensibility).

SUMMARY OF THE INVENTION

The present invention provides a copolymer from which can be manufactured an absorbable surgical article, particularly a monofilament suture possessing the desired characteristics of flexibility, resulting in good handling properties, and biodegradability. Such is achieved, according to the invention, through the modification of polyglycolic acid polymer to produce a copolymer, the extruded fibers of which exhibit a lower tensile modulus than monofilaments of polyglycolic acid alone, resulting in increased flexibility. The copolymers are bioabsorbable.

The copolymers of this invention are multiblock copolymers produced by introducing poly(alkylene glycol) blocks into poly(glycolic acid), through the transesterification of poly(glycolic acid) with an hydroxyl-ended poly(alkylene glycol) and with the degree of polymerization of the copolymer being increased by the subsequent addition of an aromatic orthocarbonate resulting in chain extension and reduction of brittleness. A preferred poly(alkylene glycol) is poly(oxyethylene) while a preferred orthocarbonate is tetra-p-tolyl orthocarbonate.

The copolymers have the following general formula:

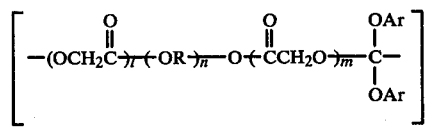

where R represents an alkylene group and Ar is an aromatic group and the poly(glycolic acid) content is about 80 to 85 percent and the poly(oxyalkylene) content is about 20 to 15 percent l and m are the same or a different positive integer, and n is 23 to 91.

Thus, an object of this invention is the provision of a poly(glycolc acid)/poly(oxyalkylene)multiblock copolymer.

A further object of this invention is the provision of a method of polymerization and aromatic orthocarbonate addition for producing the poly(glycolic acid)/poly(oxyalkylene) block copolymer.

The copolymers of the invention find advantageous utility in the manufacture of surgical articles and pharmaceutical compositions as is known in the art for polymer absorbable in living animals. Thus, yet further objects of this invention include the provision of a sterile surgical article, a suture or ligature, particularly in the form of flexible monofilaments, a suture in the form of a needle and a suture combination, a surgical clip or staple, a surgical prosthesis, textile structures, couplings, tubes or other forms of support or a self-supporting film, hollow tube, beads or gel, containing a uniformly dispersed drug for controlled continuous administration, manufactured from a copolymer, or by a method described above.

The foregoing and other objects, features and advantages of this invention will be further apparent from the following description of preferred embodiments thereof and from the claims appended hereto.

DESCRIPTION OF THE PREFERRED EMBODIMENTS

The multiblock copolymers of this invention are obtained by transesterification of poly(glycolic acid) and an hydroxyl-ended poly(alkylene glycol) such as poly(oxyethylene) in the presence of a catalyst to produce, it is theorized, an intermediate ABA copolymer:

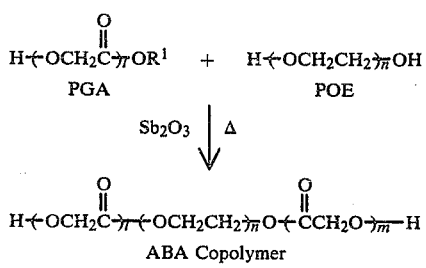

The degree of polymerization of the ABA copolymer is increased by the addition of an aromatic orthocarbonate, such as tetra-p-tolyl orthocarbonate, to yield an $(AB)_n$ type multiblock copolymer:

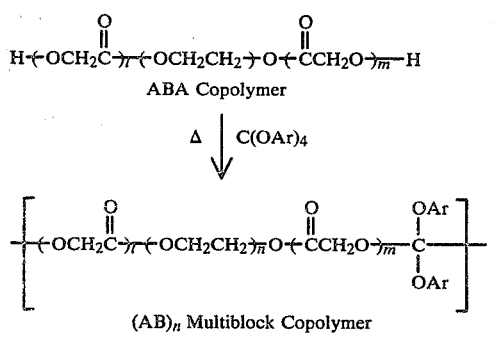

The hydroxyl-ended poly (alkylene glycol) useful in the invention may advantageously comprise hydroxyl-ended polyethylene oxide, polypropylene oxide and poly(oxyethylene-co-oxypropylene). Generally the poly(alkylene) oxides must be water soluble so that they can be excreted by the body once the copolymer suture has degraded. Examples of poly(alkylene glycols) capable of producing linear polymers are poly(oxyethylene glycols) and poly(oxypropylene)-poly (oxyethylene)-glycols (block copolymers). The foregoing are commercially available in a variety of molecular weights. Examples of suitable aromatic orthocarbonates are set forth in U.S. Pat. No. 3,174,125.

The following examples are illustrative of the invention:

EXAMPLE 1

Preparation of 85/15 ABA Copolymer

Dried polyglycolic acid (PGA) pellets, 33 g, were melted in a Brabender mixing head at 235° C. under $N_2$. A mixture of 5.8 g poly(oxyethylene) (Mol. Wt. 4000) and 35 mg. of $Sb_2O_3$ was added and mixing was continued for 30 minutes. The reactor was disassembled and the molten polymer was solidified in a stream of $N_2$, crushed in a press, ground to 10 mesh in a Wiley mill, and dried in vacuum. A small sample was purified by reprecipitation from hexafluoroacetone sesquihydrate (HFAS) into acetone.

EXAMPLE 2

Preparation of 80/20 ABA Copolymer

The procedure of Example 1 was followed using 32 g, PGA, 8 g poly(oxyethylene) of Mol. Wt. 4000, and 35 mg $Sb_2O_3$.

EXAMPLE 3

Preparation of 92.5/7.5 ABA Copolymers

The procedure of Example 1 was followed using 37 g PGA, 3 g poly(oxyethylene) of Mol. Wt. 1000, and 40 mg $Sb_2O_3$.

EXAMPLE 4

Preparation of 85/15 Multiblock $(AB)_n$ Copolymers

A mixture of 32 g dried PGA pellets, 5.7 g of poly(oxyethylene) (Mol. Wt. 4000), and 35 mg. of $Sb_2O_3$ was melted at 235° under $N_2$ in a Brabender mixing head. Mixing was continued for 30 minutes at which point 1.0 g of tetra-p-tolylorthocarbonate was added. Mixing was continued for another 2 minutes and the apparatus was disassembled and the polymer quenched in a stream of $N_2$.

EXAMPLE 5

Preparation of 80/20 Multiblock $(AB)_n$ Copolymers

The procedure of Example 4 was repeated using 32 g PGA, 8 g poly(oxyethylene) Mol. Wt. 4000 and 35 mg. of $Sb_2O_3$. After 30 minutes mixing at 235°, 1 g of tetra-p-tolylorthocarbonate was added and mixing was continued for 4 minutes. The apparatus was then disassembled and the polymer quenched in a stream of $N_2$.

The properties of the block copolymers produced according to the above examples, compared to those of polyglycolic acid above, are set forth in Table I.

TABLE I

| | Properties of PGA/POE Block Copolymers* | | | | | |
|---|---|---|---|---|---|---|
| Example | Mol. Wt. of POE | Wt. % POE Charged | Wt. % POE by NMR | $\eta$ inh (HFAS) | Tg | Tm |
| 1 | 4000 | 15 | 12 | 0.47 | 29° | 217–220° |

TABLE I-continued

Properties of PGA/POE Block Copolymers*

| Example | Mol. Wt. of POE | Wt. % POE Charged | Wt. % POE by NMR | η inh (HFAS) | Tg | Tm |
|---|---|---|---|---|---|---|
| 2 | 4000 | 20 | — | 0.46 | — | — |
| 3 | 1000 | 7.5 | 6.3 | 0.43 | — | — |
| 4 | 4000 | 15 | — | 0.64 | — | — |
| 5 | 4000 | 20 | 16 | 0.54 | 24° | 219° |
| PGA | — | 0 | — | 1.07 | 43° | 218–220° |
| PGA | — | 0 | — | 0.60 | 38° | 221° |

*All Data on reprecipitated samples.

EXAMPLE 6

Injection molded dumbbells having diameters of 0.060–0.063 inches were prepared from the relatively low molecular weight ($\theta_{inh}$0.64) 85/15 PGA/PEG multiblock copolymer of Example 4 and from a control sample of polyglycolic acid homopolymer. The potential for greater flexibility with the multiblock copolymer was illustrated by three-point bending measurements on the dumbbells which showed a modulus of $4 \times 10^5$ psi (2.75 GPa) for the copolymer and a modulus of $13 \times 10^5$ psi (8.9 GPa) for the polyglycolic acid.

We claim:

1. A multiblock copolymer useful for the manufacture of bioabsorbable surgical articles comprising the formula:

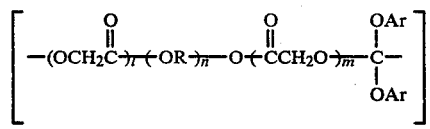

wherein R represents an alkylene group and Ar is an aromatic group, the poly(glycolic acid) content is about 80 to 85 percent, the poly(oxyalkylene) content is about 20 to 15 percent l and m are the same or a different positive integer, and n is 23 to 91.

2. A multiblock copolymer as claimed in claim 1 where R is ethylene.

3. A multiblock copolymer as claimed in claim 2 wherein the aromatic group is tetra-p-tolyl.

4. A surgical article manufactured from a copolymer as claimed in claim 1.

5. A flexible monofilament suture or ligature manufactured from a copolymer as claimed in claim 1.

6. A surgical article as claimed in claim 4 selected from the group consisting of a suture, ligature, needle and suture combination, surgical clip, surgical staple, surgical prosthesis, textile structure, coupling, tube, and support.

7. A method of making a multiblock copolymer comprising transesterifying poly(glycolic) acid and a hydroxyl-ended poly(alkylene glycol), in the presence of a catalyst, and adding to the copolymer produced thereby, an aromatic orthocarbonate to extend the chain polymerization and reduce brittleness.

8. A method as claimed in claim 7 wherein the poly(alkylene glycol) is poly(oxyethylene) and the aromatic orthocarbonate is tetra-p-tolyl orthocarbonate.

9. A surgical article manufactured from copolymer made according to a method claimed in claim 7.

10. A bioabsorbable flexible monofilament suture or ligature manufactured from copolymer made according to a method claimed in claim 7.

11. A surgical article as claimed in claim 9 selected from the group consisting of a suture, ligature, needle and suture combination, surgical clip, surgical staple, surgical prosthesis, textile structure, coupling, tube, and support.

12. A hydrolyzable monofilament fiber formed from a multiblock copolymer comprising the formula:

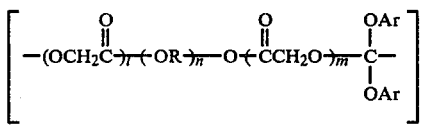

wherein R represents an alkylene group and Ar is an aromatic group, the poly(glycolic acid) content is about 80 to 85 percent, the poly(oxyalkylene) content is about 20 to 15 percent, l and m are the same or a different positive integer and n is 23 to 91, having a tensile modulus below $1 \times 10^6$ psi.

* * * * *